US009045767B2

(12) United States Patent
Bloodworth

(10) Patent No.: US 9,045,767 B2
(45) Date of Patent: Jun. 2, 2015

(54) GRAPEVINE PLANT NAMED JB05-22-3-27

(71) Applicant: SCARLET TANAGER, Lawrenceburg, IN (US)

(72) Inventor: Patterson Jeffrey Bloodworth, Hillsborough, NC (US)

(73) Assignee: SCARLET TANAGER, Lawrenceburg, IN (US)

( * ) Notice: Subject to any disclaimer, the term of this patent is extended or adjusted under 35 U.S.C. 154(b) by 0 days.

(21) Appl. No.: 14/061,322

(22) Filed: Oct. 23, 2013

(65) Prior Publication Data
US 2015/0113678 A1    Apr. 23, 2015

(51) Int. Cl.
| | |
|---|---|
| *A01H 5/00* | (2006.01) |
| *A01H 4/00* | (2006.01) |
| *C12N 15/82* | (2006.01) |
| *C12N 5/04* | (2006.01) |
| *A01H 5/08* | (2006.01) |

(52) U.S. Cl.
CPC .............. *C12N 15/8286* (2013.01); *A01H 5/08* (2013.01); *C12N 15/8245* (2013.01); *C12N 15/8247* (2013.01); *C12N 15/8274* (2013.01); *C12N 15/8282* (2013.01); *C12N 15/8283* (2013.01); *A01H 4/008* (2013.01); *C12N 5/04* (2013.01); *A01H 4/005* (2013.01); *C12N 15/8278* (2013.01); *C12N 15/8201* (2013.01); *C12N 15/8277* (2013.01); *C12N 15/8275* (2013.01); *A01H 5/0812* (2013.01)

(58) Field of Classification Search
None
See application file for complete search history.

(56) References Cited

U.S. PATENT DOCUMENTS

2011/0191897 A1 *   8/2011   Poree et al. .................... 800/278

OTHER PUBLICATIONS

Jang et al. (1997) Science 275: 218-220.*
Ramming et al. (2000) Hort Science 35: 732-734.*
Alston, et al. 1997. The California Table Grape Commission's Promotion Program: An Evaluation. Giannini Foundation Monograph No. 43. 122 p.
Bouquet, A. and M. Hevin. 1978. Green-grafting between Muscadine grape (*Vitis rotundifolia* Michx.) and bunch grapes (*Euvitis* sppl) as a tool for physiological and pathological investigations. *Vitis* 17:134-138.
Cain, et al., 1983. *In-ovulo* embryo culture and seedling development of seeded and seedless grapes (*Vitis vinifera* L.). *Vitis* 22:9-14.
Dearing, C. 1917. Muscadine Grape Breeding. J. Hered. 8:409-424.
Detjen, L. R. 1919a. The limits in hybridization of *Vitis rotundifolia* with related species and genera. N.C. Agr. Expt. Sta. Tech. Bul. 17.
Detjen, L. R. 1919b. Some F₁ Hybrids of *Vitis rotundifolia* with related species and genera. N.C. Agr. Expt. Sta. Tech. Bul. 18.
Dunstan, R. T. 1962. Some fertile hybrids of bunch and muscadine grapes. J. Hered. 53:299-303 (*Corrigendum*, 1963. 54:25).
Dunstan, R. T. 1964. Hybridization of *Euvitis* x *Vitis rotundifolia*: backcrosses to muscadine. Proc. Am. Soc. Hort. Sci. 84:238-242.
Emershad, R. L. and D. W. Ramming. 1984. In-ovulo embryo culture of *Vitis vinifera* L. C.V. 'Thompson Seedless'. Am. J. Bot. 71:873-877.
Fry, B. O. 1964. Fertile interspecific hybrids *Vitis rotundifolia* x *Vitis vinifera*. Ga. Agr. Expt. Sta. Mimeo. Series N.S. 200.
Goldy, et al. 1988. Embryo culture as a means of introgressing seedlessness from *Vitis vinifera* to *V. rotundifolia*. HortScience 23:886-889.
Goldy, R. G. 1992. Breeding Muscadine Grapes. Horticultural Reviews 14:357-405.
Jelenkovic, G., and H. P. Olmo 1968. Cytogenetics of *Vitis* III. Partially fertile F₁ diploid hybrids between *V. vinifera* x *V. rotundifolia* Michx. *Vitis* 7:281-293.
Jelenkovic, G., and H. P. Olmo 1969. Cytogenetics of *Vitis* IV. Backcross derivatives of *V. vinifera* x *V. rotundifolia* Michx. *Vitis* 8:1-11.
Ledbetter, C. A. and D. W. Ramming. 1989. Seedlessness in Grapes. Horticultural Reviews 11:159-184.
Lu, et al. 1993. Introgression of seedlessness from bunch grapes into muscadine grapes. Proc. Fla. State Hort. Soc. 106:122-124.
Lu, J. and O. Lamikanra. 1996. Barriers to intersubgeneric crosses between *Muscadinia* and *Euvitis*. HortScience 31:269-271.
Lu, J. 2001. The Grape Genetics, Breeding and Viticulture Program, Center for Viticulture! Sciences, Florida A&M University. Report to SERA-IEG14 Group. 10 p.
Merdinoglu, et al. 2002. Genetic Analysis of Downy Mildew Resistance derived from *Muscadinia rotundifolia*. ISHS Acta Horticulturae 603: VIII International Symposium on Grape Genetics and Breeding.
Olmo, H. P. 1971. *Vinifera rotundifolia* hybrids as wine grapes. Am. J. Enol. *Vitic.* 22:87-91.

(Continued)

Primary Examiner — Anne Kubelik
Assistant Examiner — Steven Bernacki
(74) Attorney, Agent, or Firm — Jondle & Associates, P.C.

(57) ABSTRACT

A grapevine cultivar designated JB05-22-3-27 is disclosed. The invention relates to the plants of grapevine cultivar JB05-22-3-27, to the plant parts of grapevine cultivar JB05-22-3-27 and to methods for producing a grapevine plant produced by crossing grapevine cultivar JB05-22-3-27 with itself or with another grapevine variety. The invention also relates to methods for producing a grapevine plant containing in its genetic material one or more transgenes and to the transgenic grapevine plants and plant parts produced by those methods. This invention also relates to grapevine cultivars or breeding cultivars and plant parts derived from grapevine variety JB05-22-3-27, to methods for producing other grapevine cultivars, lines or plant parts derived from grapevine cultivar JB05-22-3-27 and to the grapevine plants, varieties, and their parts derived from use of those methods. The invention further relates to hybrid grapevine fruits, seeds, plants and plant parts produced by crossing grapevine cultivar JB05-22-3-27 with another grapevine cultivar.

18 Claims, No Drawings

(56) References Cited

OTHER PUBLICATIONS

Patel, G. I. and H. P. Olmo. 1955. Cytogenetics of *Vitis: I*. The hybrid *V. vinifera* x *V. rotundifolia*. Amer. J. Bot. 42:141-159.

Qu, et al. 1996. Genetic diversity in Muscadine and American bunch grapes based on randomly amplified polymorphic DNA (RAPD) analysis. J. Amer. Soc. Hort. Sci. 121(6):1020-1023.

Ramming, et al. 2000. A stenospermocarpic, seedless *Vitis vinifera* x *Vitis rotundifolia* hybrid developed by embryo rescue. HortScience 35:732-734.

Ramming, et al. 2012. Identification of Race-Specific Resistance in North American *Vitis* spp. Limiting *Erysiphe necator* Hyphal Growth. Phytopathology 102:83-93.

Riaz, et al. 2011. Using a limited mapping strategy to identify major QTLs for resistance to grapevine powdery mildew (*Erysiphe necator*) and their use in marker-assisted breeding. Theor. Appl. Genet. 122:1059-1073.

Spiegel-Roy, et al. 1985. In vitro culture and plant formation from grape cultivars with abortive ovules and seeds. J. Am. Soc. Hort. Sci. 110:109-112.

* cited by examiner

GRAPEVINE PLANT NAMED JB05-22-3-27

BACKGROUND OF THE INVENTION

This present invention relates to a new and distinctive grapevine cultivar, designated JB05-22-3-27. All publications cited in this application are herein incorporated by reference.

The goal of plant breeding is to combine in a single variety or hybrid various desirable traits. For fruiting crops, such as grapes (*Vitis*), these traits may include resistance to diseases and insects, tolerance to heat and cold, greater yield, better viticultural quality, high concentrations of anti-oxidant phytochemicals, ease of hand or mechanical harvesting of berries, uniform berry size and color, and pleasant aroma and flavor.

Grapes botanically belong to the family Vitaceae, which is divided into 16 genera. Of these, *Vitis* is the only genus with economic importance. The genus *Vitis* is divided into two subgenera, *Euvitis* Planch. and *Muscadinia* Planch. The subgenus *Euvitis* has 38 chromosomes and many berries borne in each cluster so that the general term 'bunch grape' is given to all species of *Euvitis*. *Muscadinia* has 40 chromosomes and smaller clusters, with a common name of muscadine grape.

More than 60 species have been described in *Euvitis*, including hundreds of known cultivars. *Vitis vinifera* L. is the predominant commercial species of *Euvitis*, which is grown all over the world and has given rise to thousands of cultivars. Cultivars of *V. vinifera* form the basis of the majority of wines produced around the world. *V. vinifera* vines often suffer from limited cold hardiness and are susceptible to pests and diseases such as grape root aphid, phylloxera, Pierce's Disease, and the fungal diseases powdery mildew, black rot, and downy mildew. *Vitis rotundifolia*, normally referred to as the muscadine grape, is the only species within *Muscadinia* with commercial value. Muscadine grapes have many outstanding qualities, including: 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, and 5) distinctive, pleasant floral aroma and flavor.

The genus *Vitis* is economically important as the source of grapes, both for direct consumption of the fruit and for fermentation to produce wine. Commercially cultivated grapes can be classified as either table grapes, which are eaten raw, or wine grapes for wine production. While almost all grapes belong to the same species, *Vitis vinifera*, table and wine grapes have significant differences, brought about by selective breeding. Table grape plants tend to have large, seedless fruit with thin skin, whereas wine grapes are smaller with seeds and rather thick skins. Grapes can also be used for making jam, juice, jelly, grape seed extract, raisins, vinegar, and grape seed oil.

Antioxidants found in grapes are believed to have protective health benefits. The compound resveratrol is believed to aid in reducing propensity to vascular damage and blood pressure, among other health benefits. Resveratrol is found in varying amounts among grape varieties, primarily in their skins and seeds, which, in muscadine grapes have about one hundred times higher concentration than the pulp. Total phenolic content, which is a laboratory index of antioxidant strength, is higher in purple varieties due to anthocyanin density in purple grape skin compared to the absence of anthocyanins in white grape skin. Anthocyanins and other pigment chemicals of the larger family of polyphenols in purple grapes are responsible for the varying shades of purple in red wines. Anthocyanins are also believed to have benefits for human health. In addition, grape seed extract has been suggested to have potential anticancer effects and grape seed oil is notable for its high contents of phytosterols, polyunsaturated fatty acids such as linoleic acid, oleic acid and alpha-linolenic acid.

Seedless grape cultivars are increasingly available and now make up the majority of *Vitis vinifera* table grape plantings. Grapevines are vegetatively propagated by cuttings and the lack of seeds poses difficulties for grape breeders, who must either use a seeded variety as the female parent or recue embryos early in development using tissue culture techniques. Although seedless table grapes offer improved eating quality, a disadvantage is the loss of the potential health benefits provided by the enriched phytochemical content of grape seeds.

Therefore, it is desirable to develop a novel table grape that combines the seedless characteristic of *V. vinifera* table grapes with the superior characteristics of the muscadine grape to develop a seedless muscadine grape variety having superior qualities.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new grapevine cultivar designated JB05-22-3-27. This invention thus relates to grapevine cultivar JB05-22-3-27, to the plants and plant parts of grapevine cultivar JB05-22-3-27 and to methods for producing a grapevine plant produced by crossing grapevine cultivar JB05-22-3-27 with itself or another grapevine variety, and the creation of variants by mutagenesis, cell culture or transformation of grapevine cultivar JB05-22-3-27 or other methods of transference of JB05-22-3-27 genetic material, traits or attributes.

This invention also relates to methods for introgressing a transgenic or mutant trait into grapevine cultivar JB05-22-3-27 and to the grapevine plants and plant parts produced by those methods. This invention also relates to grapevine cultivars or breeding cultivars and plant parts derived from grapevine cultivar JB05-22-3-27, to methods for producing other grapevine cultivars or plant parts derived from grapevine cultivar JB05-22-3-27 and to the grapevine plants, varieties, and their parts derived from the use of those methods. This invention further relates to grapevine seeds, plants, and plant parts produced by crossing grapevine cultivar JB05-22-3-27 with another grapevine cultivar. Thus, any such methods using the grapevine cultivar JB05-22-3-27 are part of this invention: selfing, backcrosses, hybrid production, crosses to populations, and the like. All plants produced using grapevine cultivar JB05-22-3-27 as at least one parent are within the scope of this invention. Advantageously, the grapevine cultivar could be used in crosses with other, different, grapevine plants to produce first generation ($F_1$) grapevine hybrid plants with superior characteristics.

In another aspect, the present invention provides regenerable cells for use in tissue culture of grapevine plant JB05-22-3-27. The tissue culture will preferably be capable of regenerating plants having all the physiological and morphological characteristics of the foregoing grapevine plant, and of regenerating plants having substantially the same genotype as the foregoing grapevine plant. Preferably, the regenerable cells in such tissue cultures will be embryos, protoplasts, meristematic cells, callus, pollen, leaves, ovules, anthers, cotyledons, hypocotyl, pistils, roots, root tips, flowers, seeds, petiole, pods, or stems. In another aspect of the present invention, embryos resulting from pollinations are isolated by embryo rescue. Still further, the present invention provides grapevine plants regenerated from the tissue cultures of the invention.

In addition to the exemplary aspects and embodiments described above, further aspects and embodiments will become apparent by study of the following descriptions in conjunction with the accompanying tabular data; and, it is to be expressly understood that these descriptions and data are for the purpose of illustration and/or description and is not intended as a definition of the limits of the invention.

DETAILED DESCRIPTION OF THE INVENTION

In the description and tables that follow, a number of terms are used. In order to provide a clear and consistent understanding of the specification and claims, including the scope to be given such terms, the following definitions are provided:

Allele. The allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Calyptra. The corolla of the grape flower whose petals are fused at the distal end and which abscise at the proximal end, forming a cap which sheds at flowering.

Crossing. The pollination of a female flower of a grape plant, thereby resulting in the production of seed from the flower.

Cross-pollination. Fertilization by the union of two gametes from different plants.

Desired phenotypic traits. As used herein, refers to the desired phenotypic traits of a muscadine grape plant, including the recently developed traits of tender, crunchy skin and meaty/melting flesh. Desired phenotypic traits of muscadine also include the outstanding qualities of 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, 5) distinctive, pleasant floral aroma and flavor and 6) naturally large and attractive berries.

Embryo. The young plant individual after fertilization or parthenogenesis when the proembryo has differentiated into embryo and suspensor.

Embryo culture. The growth of isolated plant embryos on suitable media in vitro.

Embryo rescue. As used herein, embryo rescue is the process plant breeders use to attempt to germinate embryos that may be weak, immature, or would otherwise not develop into a mature viable seed on the parent plant.

Essentially all the physiological and morphological characteristics. A plant having essentially all the physiological and morphological characteristics means a plant having the physiological and morphological characteristics, except for the characteristics derived from the converted gene.

Extended-bearing. Normally, grapevines produce 2 or 3 inflorescences/clusters per primary shoot from primary buds. The floral primordia that give rise to these inflorescences are formed in developing primary buds in the season prior to their emergence. Some non-intersubgeneric genotypes produce 2 and rarely 3 inflorescences/clusters per lateral shoot in the current season. This is often referred to as a secondary crop that lags slightly behind the primary crop in ripening. Intersubgeneric hybrid vines that have an everflowering trait (EF), on primary and lateral shoots, continually produce inflorescences in the current season instead of tendrils, which are grasping structures thought to be evolutionarily derived from inflorescences. Consequently, there is a continuous succession of inflorescence production, flowering, fruit set, development and ripening along a shoot as long as it continues to grow. The season of bearing is thus extended. Hybrid genotypes vary in the extent to which inflorescences continue to be formed instead of tendrils. In the extreme case, inflorescences are produced to the exclusion of tendrils until the very end of the growing season when frost occurs.

Female fertile. Female fertile plants produce viable seeds or at least culturable embryos, and can include hermaphrodite plants.

Hermaphrodite. An organism having both male and female reproductive organs.

Muscadine. Botanically know as *Vitis rotundifolia*, muscadine is a grapevine species native to the Southeastern United States. Muscadine grapes have a number of outstanding qualities, including 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, 5) distinctive, pleasant floral aroma and flavor and 6) naturally large and attractive berries. Muscadine grapes are typically consumed fresh and are used to make wine, juice and jelly.

Parthenocarpy. The natural or artificially induced production of fruit without fertilization of ovules. Parthenocarpic fruit is therefore seedless.

Plant cell. Plant cell, as used herein includes plant cells whether isolated, in tissue culture, or incorporated in a plant or plant part.

Plant part. As used herein, the term "plant part" includes, but is not limited to, leaves, stems, roots, seeds, embryos, pollens, ovules, flowers, berries, stalks, root tips, tissue, cells and the like.

Pollination. Pollination is the process by which pollen is transferred in plants, thereby enabling fertilization and sexual reproduction.

Quantitative Trait Loci (QTL) Quantitative trait loci refer to genetic loci that control to some degree numerically representable traits that are usually continuously distributed.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Stenospermocarpy (SSC). A heritable trait that induces cessation in development of ovules into potential seeds, even though fertilization has taken place. Variable timing of this cessation results in recognizable but limited development of seed structures, including the seed coat and endosperm, although the embryo may or may not continue to develop. The remains of the undeveloped seed can be seen in the fruit, which continues to develop and ripen. As used herein, 1.58 mm in length is the cut off for the smallest aborted seed trace with opaque pigmentation (green, red or brown), and any such trace with a greater measure than 1.58 mm in length is an example of stenospermocarpy. Not all of the typically 4 ovules per flower need to be fertilized to form a stenospermocarpic fruit, and usually, unfertilized and undeveloped ovules can be found along with seed traces in such fruits. Stenospermic vines can produce some seedless, parthenocarpic fruits, which are smaller than stenospermocarpic fruits, but none of the ovules ever show evidence of fertilization and remain small, translucent and white in color.

Transgene. A genetic sequence which has been introduced into the nuclear or chloroplast genome of a corn plant by a genetic transformation technique.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants)

Grapevine cultivar JB05-22-3-27 of the present invention is a *Vitis* intersubgeneric hybrid of *Muscadinia* and *Euvitis* that produces seedless berries. JB05-22-3-27 continuously produces inflorescences instead of tendrils throughout the season on all shoots and sets full berry clusters with a mixture of small parthenocarpic berries up to $6/16"\times6/16"$ and stenospermic berries up to $12/16"\times9/16"$. Berries of JB05-22-3-27 are of excellent quality for eating whole when fully ripe and dark red to purple. The berries resist cracking and rot after heavy rains, but late in the season scattered ripe rot is seen on overripe berries. Very ripe berries late in the season are attractive to bees which can easily puncture the thin tender skin, so unless protected, all ripe fruit should be regularly harvested.

Grapevine cultivar JB05-22-3-27 has shown uniformity and stability, as described in the following variety description information. It has been propagated and the propagule has fruited for several years and is identical in all respects to the original plant. The line has been increased with continued observation for uniformity.

The following data was collected in August, September and October of 2013, except for time of flowering and bud burst, which were collected at appropriate times in prior years. The plant used in this description was eight-years old and field grown. Color terminology follows the Royal Horticultural Society Colour Chart, London (RHS) ($5^{th}$ edition). Grapevine variety JB05-22-3-27 has the following morphologic and other characteristics (based primarily on data collected in Hillsborough, N.C.).

TABLE 1

VARIETY DESCRIPTION INFORMATION

Genus species: *Vitis* intersubgeneric hybrid of *Muscadinia* and *Euvitis*
Plant:
   Habit: Recumbent, climbing
   Age at maturity: 3 years
   Height (at maturity): 6 ft
   Width (at maturity): 4 ft
   Vigor: High
   Productivity: High
   Rootstock: Own-rooted
Trunk:
   Diameter: 1 5/8"
   Surface texture: Smooth to rough
   Color:
     Bark: RHS 197C (Greyed-green group)
     Freshly exposed wood: RHS 177C (Greyed-orange group)
Canes:
   Diameter: 9/32" × 7/32", measured at middle of third proximal internode of
   mature cane
   Length: Up to 10 ft
   Surface texture (mature cane): Smooth, with slightly raised erumpent corky
   lenticels
   Form (woody shoot cross section): Elliptical
   Color:
     Mature: Predominant color RHS 177B (Greyed-orange group) with
     darker striations of RHS 175A (Greyed-orange group)
     Immature: RHS 146C (Yellow-green group) before lenticels become
     corky
   Internode length: Average 2 ½"
   Time of bud burst:
     Swollen buds: Apr. 8
     Swollen buds with visible green tissue: Apr. 14
     Fully burst: Apr. 17
Tendrils:
Note: Tendrils are not produced in abundance as most develop into inflorescences
   Form: Bifid
   Length: Up to 6 ½"
   Diameter: 1/32"
   Texture: Smooth TABLE 1-continued

VARIETY DESCRIPTION INFORMATION

Color:
  Mature: RHS 152A (Yellow-green group) overlaid with RHS 178A
  (Greyed-red group) striae. Tendril branches largely RHS 178A (Greyed-
  red group)
  Immature: RHS 163C (Greyed-orange group) with RHS 178A (Greyed-
  red group) to RHS 184A (Greyed-purple group) on sun-exposed side
Growing tips:
  Pubescence: Present
  Pubescence color (on adaxial surface of young leaves): RHS 63C (Red-purple
  group)
  Color:
    Young shade stems: RHS 146A (Yellow-green group)
    Young sun stems: RHS 64A (Red-purple group), RHS 184A (Greyed-
    purple group), RHS 187A (Greyed-purple group)
Leaves:
  Shape: Orbicular
  Apex: Pointed
  Base: Sagittate
  Margin: Dentate
  Length of teeth on margin: 3 8/32"
  Shape of teeth on margin: Dentate, pointed, and mainly straight-sided with
  occasional tendency to concavity or convexity
  Texture (mature leaf):
    Upper surface: Smooth
    Lower surface: Smooth
  Size (immature):
    Length: 1 1/2"
    Width: 1 1/4"
  Size (mature):
    Length: 5 1/4"
    Width: 4 7/8"
  Color (immature):
    Upper surface: RHS 146B (Yellow-green group)
    Lower surface: RHS 146C (Yellow-green group)
  Color (mature):
    Upper surface: RHS 137A (Green group)
    Lower surface: RHS 137B (Green group)
  Venation pattern: Palmate
  Venation color:
    Upper surface: RHS 146C (Yellow-green group)
    Lower surface: RHS 147C, 146D (Yellow-green group)
  Petiolar sinus: Open, lyre-shaped
  Petiole:
    Length: Up to 4 7/8"
    Diameter: 1/16"
    Color: RHS 144A (Yellow-green group) with greyed-red group adjacent
    to leaf and on sun-exposed side
Floral cluster:
General description and location: On stems opposite leaves except at every third node.
This vine normally produces inflorescences instead of tendrils throughout the growing
season, with as many as 24 inflorescences on vigorous primary shoots.
  Quantity of florets per inflorescence: 125
  Inflorescence length: Average approximately 1 1/2"
  Inflorescence width: Average approximately 1"
  Peduncle length: 1"
  Sex: Hermaphroditic
  Stamens: Upright
  Anthers color (freshly dehisced): RHS 18B (Yellow-orange group)
  Date of bloom: Earliest noted Jun. 6
  Pollen amount: Abundant
  Calyptra: Sheds normally
  Calyptra color: RHS N144D (Yellow-green group) just before shed; RHS 152D
  (Yellow-green group) just shed
Fruit:
Note: Both stenospermic and parthenocarpic berries are regularly produced
  Time of year of optimal ripeness: Beginning mid-September
  Cluster:
    Size: Small
    Length (without peduncle): Approximately up to 3"
    Width: Approximately up to 2"
    Number of berries per cluster: 10-100, average about 50
  Peduncle:
    Length: 1 1/2" to 2"
    Diameter: 1/16"
    Color: From RHS 152C (Yellow-green group) to RHS 165A (Greyed-
    orange group)
  Berry:
    Size: Small

TABLE 1-continued

VARIETY DESCRIPTION INFORMATION

Uniformity: This vine produces a mixture of approximately 1/3 parthenocarpic berries and 2/3 stenospermic berries
Parthenocarpic berries:
  Shape: Spherical
  Size: 10/32" long × 10/32" wide to 12/32" long × 12/32" wide
Stenospermic berries:
  Shape: Elliptical to ovate, rarely oblate
  Size: 13/32" long × 11/32" wide up to 24/32" long × 18/32" wide, depending on the number and size of partially developed ovules, which can reach a length exceeding 1.88/16" (1.5 mm) to a maximum length of 5.4/32" (4.3 mm)
  Ovules: Remain soft and are unnoticeable during consumption
Brix content (near ripe): 15.0°
Brix content (ripe): 18.5°
Flavor (ripe): Mildly floral, lacking musky character of *V. rotundifolia*
Skin. 1/32" thick, not adherent to flesh, crunchy, tender, resistant to cracking
Skin color (near ripe): RHS 185A (Greyed-purple group)
Skin color (ripe): RHS N77A (Purple group)
Flesh: Mucilaginous, juicy
Juice color: Clear
Pedicel:
  Length: 3 4/32"
  Diameter (stenospermic): 1/32"
  Diameter (parthenocarpic): 1/64"
  Color: RHS 152D (Yellow-green group)
  Strength of attachment to stenospermic berry: Moderately strong, ½ detach with pedicel, which breaks
  Strength of attachment to parthenocarpic berry: Moderate to weak, ½ detach with pedicel, which breaks
  Secondary bunches: Produced on lateral shoots as on primary shoots with similar characteristics
Disease and insect resistance:
  Downy mildew: Highly resistant
  Powdery mildew: Highly resistant on vine and fruit
  Angular leaf spot: Highly resistant
  Target spot (zonate leaf spot): Susceptible, but only a factor in very wet years
  Attractive to Japanese Beetles This invention is also directed to methods for producing a grapevine plant by crossing a first parent grapevine plant with a second parent grapevine plant, wherein the first or second grapevine plant is the grapevine plant from cultivar JB05-22-3-27. Further, both first and second parent grapevine plants may be from cultivar JB05-22-3-27. Therefore, any methods using grapevine cultivar JB05-22-3-27 are part of this invention: selfing, backcrosses, hybrid breeding, and crosses to populations. Any plants produced using grapevine cultivar JB05-22-3-27 as at least one parent are within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

The fruit of grapevine cultivar JB05-22-3-27, the plant produced from the fruit, the hybrid grapevine plant produced from the crossing of the variety with any other grapevine plant, hybrid fruit and seed, and various parts of the grapevine plant can be utilized for human food, such as table grapes. The grapes can be whole grapes (fresh or frozen), raisins, fruit leather, paste, puree, freeze-dried fruits, nutraceutical preparations, wine, juice, jam and jelly.

FURTHER EMBODIMENTS OF THE INVENTION

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, which are introduced into the genome using transformation or various breeding methods are referred to herein collectively as "transgenes." In some embodiments of the invention, a transgenic variant of grapevine cultivar JB05-22-3-27 may contain at least one transgene but could contain at least 1, 2, 3, 4, 5, 6, 7, 8, 9, 10, and/or no more than 15, 14, 13, 12, 11, 10, 9, 8, 7, 6, 5, 4, 3, or 2. Over the last 15 to 20 years several methods for producing transgenic plants have been developed, and the present invention also relates to transgenic variants of the claimed grapevine cultivar JB05-22-3-27.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least approximately 1000 nucleotides of sequence upstream from the 5' end of the coding region and at least approximately 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

One embodiment of the invention is a process for producing grapevine cultivar JB05-22-3-27 further comprising a desired trait, said process comprising introducing a transgene that confers a desired trait to a grapevine plant of cultivar JB05-22-3-27. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including: a polynucleotide conferring resistance to imidazolinone, dicamba, sulfonylurea, glyphosate, glufosinate, triazine, benzonitrile, cyclohexanedione, phenoxy proprionic acid, and L-phosphinothricin; a polynucleotide encoding a *Bacillus thuringiensis* polypeptide; a polynucleotide encoding phytase, FAD-2, FAD-3, galactinol synthase, or a raffinose synthetic enzyme; or a polynucleotide conferring resistance to grape root aphid, phylloxera, Pierce's Disease, and the fungal diseases powdery mildew, black rot, and downy mildew.

Numerous methods for plant transformation have been developed, including biological and physical plant transformation protocols. See, for example, Miki et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993), and Armstrong, "The First Decade of Maize Transformation: A Review and Future Perspective," *Maydica*, 44:101-109 (1999). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A genetic trait which has been engineered into the genome of a particular grapevine plant may then be moved into the genome of another variety using traditional breeding techniques that are well known in the plant breeding arts. For example, a backcrossing approach is commonly used to move a transgene from a transformed grapevine variety into an already developed grapevine variety, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid and can be used alone or in combination with other plasmids to provide transformed grapevine plants using transformation methods as described below to incorporate transgenes into the genetic material of the grapevine plant(s).

Expression Vectors for Grapevine Transformation: Marker Genes

Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley, et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant (Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986)). Other selectable marker genes confer resistance to herbicides such as glyphosate, glufosinate, or bromoxynil (Comai, et al., *Nature*, 317:741-744 (1985); Gordon-Kamm, et al., *Plant Cell*, 2:603-618 (1990); Stalker, et al., *Science*, 242:419-423 (1988)).

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase, and chloramphenicol acetyltransferase (Jefferson, R. A., Plant Mol. *Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

In vivo methods for visualizing GUS activity that do not require destruction of plant tissue are available (Molecular Probes, Publication 2908, IMAGENE GREEN, pp. 1-4 (1993); Naleway, et al., *J. Cell Biol.,* 115:151a (1991)). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells (Chalfie, et al., *Science,* 263: 802 (1994)). GFP and mutants of GFP may be used as screenable markers.

Expression Vectors for Grapevine Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions.

A. Inducible Promoters—An inducible promoter is operably linked to a gene for expression in grapevine. Optionally, the inducible promoter is operably linked to a nucleotide sequence encoding a signal sequence which is operably linked to a gene for expression in grapevine. With an inducible promoter the rate of transcription increases in response to an inducing agent.

Any inducible promoter can be used in the instant invention. See, Ward, et al., Plant Mol. Biol., 22:361-366 (1993). Exemplary inducible promoters include, but are not limited to, that from the ACEI system which responds to copper (Mett, et al., Proc. Natl. Acad. Sci. USA, 90:4567-4571 (1993)); In2 gene from maize which responds to benzenesulfonamide herbicide safeners (Hershey, et al., Mol. Gen Genetics, 227:229-237 (1991); Gatz, et al., Mol. Gen. Genetics, 243:32-38 (1994)); or Tet repressor from Tn10 (Gatz, et al., Mol. Gen. Genetics, 227:229-237 (1991)). A particularly preferred inducible promoter is a promoter that responds to an inducing agent to which plants do not normally respond. An exemplary inducible promoter is the inducible promoter from a steroid hormone gene, glucocorticoid response elements, the transcriptional activity of which is induced by a glucocorticoid hormone (Schena, et al., Proc. Natl. Acad. Sci. USA, 88:10421-10425 (1991)).

B. Constitutive Promoters—A constitutive promoter is operably linked to a gene for expression in grapevine or the constitutive promoter is operably linked to a nucleotide sequence encoding a signal sequence which is operably linked to a gene for expression in grapevine.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2: 163-171 (1990)); ubiquitin (Christensen, et al., Plant Mol. Biol., 12:619-632 (1989); Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)); and maize H3 histone (Lepetit, et al., Mol. Gen. Genetics, 231: 276-285 (1992); Atanassova, et al., Plant Journal, 2 (3): 291-300 (1992)). The ALS promoter, an XbaI/NcoI fragment 5' to the Brassica napus ALS3 structural gene (or a nucleotide sequence similarity to said XbaI/NcoI fragment), represents a particularly useful constitutive promoter. See PCT Application WO 96/30530.

C. Tissue-Specific or Tissue-Preferred Promoters—A tissue-specific promoter is operably linked to a gene for expression in grapevine. Optionally, the tissue-specific promoter is operably linked to a nucleotide sequence encoding a signal sequence which is operably linked to a gene for expression in grapevine. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter such as that from the phaseolin gene (Murai, et al., Science, 23:476-482 (1983); Sengupta-Gopalan, et al., Proc. Natl. Acad. Sci. USA, 82:3320-3324 (1985)); a leaf-specific and light-induced promoter such as that from cab or rubisco (Simpson, et al., EMBO J., 4(11): 2723-2729 (1985); Timko, et al., Nature, 318:579-582 (1985)); an anther-specific promoter such as that from LAT52 (Twell, et al., Mol. Gen. Genetics, 217:240-245 (1989)); a pollen-specific promoter such as that from Zm13 (Guerrero, et al., Mol. Gen. Genetics, 244:161-168 (1993)); or a microspore-preferred promoter such as that from apg (Twell, et al., Sex. Plant Reprod., 6:217-224 (1993)).

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Knox, C., et al., Plant Mol. Biol., 9:3-17 (1987); Lerner, et al., Plant Physiol., 91:124-129 (1989); Frontes, et al., Plant Cell, 3:483-496 (1991); Matsuoka, et al., Proc. Natl. Acad. Sci., 88:834 (1991); Gould, et al., J. Cell. Biol., 108:1657 (1989); Creissen, et al., Plant J., 2:129

(1991); Kalderon, et al., Cell, 39:499-509 (1984); Steifel, et al., Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is a grapevine plant. In another preferred embodiment, the biomass of interest is fruit. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, Methods in Plant Molecular Biology and Biotechnology, CRC Press, Inc., Boca Raton, 269:284 (1993). Map information concerning chromosomal location is useful for proprietary protection of a subject transgenic plant.

Wang, et al. discuss "Large Scale Identification, Mapping and Genotyping of Single-Nucleotide Polymorphisms in the Human Genome," Science, 280:1077-1082 (1998), and similar capabilities are becoming increasingly available for the grapevine genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR, and sequencing, all of which are conventional techniques. SNPs may also be used alone or in combination with other techniques.

Likewise, by means of the present invention, plants can be genetically engineered to express various phenotypes of agronomic interest. Through the transformation of grapevine, the expression of genes can be altered to enhance disease resistance, insect resistance, herbicide resistance, agronomic, grain quality, and other traits. Transformation can also be used to insert DNA sequences which control or help control male-sterility. DNA sequences native to grapevine, as well as non-native DNA sequences, can be transformed into grapevine and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Many techniques for gene silencing are well known to one of skill in the art, including, but not limited to, knock-outs (such as by insertion of a transposable element such as mu (Vicki Chandler, The Maize Handbook, Ch. 118 (Springer-Verlag 1994)) or other genetic elements such as a FRT and Lox that are used for site specific integrations, antisense technology (see, e.g., Sheehy, et al., PNAS USA, 85:8805-8809 (1988); and U.S. Pat. Nos. 5,107,065, 5,453,566, and 5,759,829); co-suppression (e.g., Taylor, Plant Cell, 9:1245 (1997); Jorgensen, Trends Biotech., 8(12):340-344 (1990); Flavell, PNAS USA, 91:3490-3496 (1994); Finnegan, et al., Bio/Technology, 12:883-888 (1994); Neuhuber, et al., Mol. Gen. Genet., 244:230-241 (1994)); RNA interference (Napoli, et al., Plant Cell, 2:279-289 (1990); U.S. Pat. No. 5,034,323; Sharp, Genes Dev., 13:139-141 (1999); Zamore, et al., Cell, 101:25-33 (2000); Montgomery, et al., PNAS USA, 95:15502-15507 (1998)), virus-induced gene silencing (Burton, et al., Plant Cell, 12:691-705 (2000); Baulcombe, Curr. Op. Plant Bio., 2:109-113 (1999)); target-RNA-specific ribozymes (Haseloff, et al., Nature, 334: 585-591 (1988)); hairpin structures (Smith, et al., Nature, 407:319-320 (2000); WO 99/53050; WO 98/53083); MicroRNA (Aukerman & Sakai, Plant Cell, 15:2730-2741 (2003)); ribozymes (Steinecke, et al., EMBO J., 11:1525 (1992); Perriman, et al., Antisense Res. Dev., 3:253 (1993)); oligonucleotide mediated targeted modification (e.g., WO 03/076574 and WO 99/25853); Zn-finger targeted molecules (e.g., WO 01/52620, WO 03/048345, and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with one or more cloned resistance genes to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); Mindrinos, et al., Cell, 78:1089 (1994) (*Arabidopsis* RSP2 gene for resistance to *Pseudomonas syringae*); McDowell & Woffenden, Trends Biotechnol., 21(4):178-83 (2003); and Toyoda, et al., Transgenic Res., 11 (6):567-82 (2002).

B. A *Bacillus thuringiensis* protein, a derivative thereof or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

C. A lectin. See, for example, Van Damme, et al., Plant Molec. Biol., 24:25 (1994), who disclose the nucleotide sequences of several *Clivia miniata* mannose-binding lectin genes.

D. A vitamin-binding protein such as avidin. See, PCT Application US 93/06487, which teaches the use of avidin and avidin homologues as larvicides against insect pests.

E. An enzyme inhibitor, for example, a protease or proteinase inhibitor or an amylase inhibitor. See, for example, Abe, et al., J. Biol. Chem., 262:16793 (1987) (nucleotide sequence of rice cysteine proteinase inhibitor); Huub, et al., Plant Molec. Biol., 21:985 (1993) (nucleotide sequence of cDNA encoding tobacco proteinase inhibitor I); Sumitani, et al., Biosci. Biotech. Biochem., 57:1243 (1993) (nucleotide sequence of *Streptomyces nitrosporeus* α-amylase inhibitor); and U.S. Pat. No. 5,494,813 (Hepher and Atkinson, issued Feb. 27, 1996).

F. An insect-specific hormone or pheromone, such as an ecdysteroid or juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor); Pratt, et al., Biochem. Biophys. Res. Comm., 163:1243 (1989) (an allostatin is identified in *Diploptera puntata*); Chattopadhyay, et al., Critical Reviews in Microbiology, 30(1):33-54 (2004); Zjawiony, J Nat Prod, 67(2):300-310 (2004); Carlini & Grossi-de-Sa, Toxicon, 40(11):1515-1539 (2002); Ussuf, et al., Curr Sci., 80(7):847-853 (2001); Vasconcelos & Oliveira, Toxicon, 44(4):385-403 (2004). See also, U.S. Pat. No. 5,266,317 to Tomalski, et al., which discloses genes encoding insect-specific, paralytic neurotoxins.

H. An insect-specific venom produced in nature by a snake, a wasp, etc. For example, see, Pang, et al., Gene, 116:165 (1992), for disclosure of heterologous expression in plants of a gene coding for a scorpion insectotoxic peptide.

I. An enzyme responsible for a hyperaccumulation of a monoterpene, a sesquiterpene, a steroid, hydroxamic acid, a phenylpropanoid derivative, or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See, PCT Application WO 93/02197 (Scott, et al.), which discloses the nucleotide sequence of a callase gene. DNA molecules which contain chitinase-encoding sequences can be obtained, for example, from the ATCC under Accession Nos. 39637 and 67152. See also, Kramer, et al., Insect Biochem. Molec. Biol., 23:691 (1993), who teach the nucleotide sequence of a cDNA encoding tobacco hornworm chitinase, and Kawalleck, et al., Plant Molec. Biol., 21:673 (1993), who provide the nucleotide sequence of the parsley ubi4-2 polyubiquitin gene, U.S. Pat. Nos. 7,145,060, 7,087,810, and 6,563,020.

K. A molecule that stimulates signal transduction. For example, see the disclosure by Botella, et al., Plant Molec. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

L. A hydrophobic moment peptide. See, PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance.

M. A membrane permease, a channel former or a channel blocker. For example, see the disclosure of Jaynes, et al., *Plant Sci*, 89:43 (1993), of heterologous expression of a cecropin-β lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., *Ann. Rev. Phytopathol.*, 28:451 (1990). Coat protein-mediated resistance has been conferred upon transformed plants against alfalfa mosaic virus, cucumber mosaic virus, and tobacco mosaic virus.

O. An insect-specific antibody or an immunotoxin derived therefrom. Thus, an antibody targeted to a critical metabolic function in the insect gut would inactivate an affected enzyme, killing the insect. See, Taylor, et al., Abstract #497, Seventh Int'l Symposium on Molecular Plant-Microbe Interactions (Edinburgh, Scotland 1994) (enzymatic inactivation in transgenic tobacco via production of single-chain antibody fragments).

P. A virus-specific antibody. See, for example, Tavladoraki, et al., Nature, 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See, Lamb, et al., *Bio/Technology*, 10:1436 (1992). The cloning and characterization of a gene which encodes a bean endopolygalacturonase-inhibiting protein is described by Toubart, et al., *Plant J.*, 2:367 (1992).

R. A developmental-arrestive protein produced in nature by a plant. For example, Logemann, et al., *Bio/Technology*, 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., *Current Biology*, 5(2) (1995); Pieterse & Van Loon, *Curr. Opin. Plant Bio.*, 7(4):456-64 (2004); and Somssich, *Cell*, 113(7):815-6 (2003).

T. Antifungal genes. See, Cornelissen and Melchers, *Plant Physiol.*, 101:709-712 (1993); Parijs, et al., *Planta*, 183:258-264 (1991); and Bushnell, et al., *Can. J. of Plant Path.*, 20(2): 137-149 (1998). See also, U.S. Pat. No. 6,875,907.

U. Detoxification genes, such as for fumonisin, beauvericin, moniliformin, and zearalenone and their structurally-related derivatives. See, for example, U.S. Pat. No. 5,792,931.

V. Cystatin and cysteine proteinase inhibitors. See, U.S. Pat. No. 7,205,453.

W. Defensin genes. See, WO 03/000863 and U.S. Pat. No. 6,911,577.

Any of the above-listed disease or pest resistance genes (A-W) can be introduced into the claimed grapevine cultivar through a variety of means including, but not limited to, transformation and crossing.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Mild, et al., *Theor. Appl. Genet.*, 80:449 (1990), respectively.

B. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT) and *Streptomyces hygroscopicus* PAT bar genes), pyridinoxy or phenoxy proprionic acids, and cyclohexanediones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587, 6,338,961, 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287, and 5,491,288; and International Publications EP1173580, WO 01/66704, EP1173581, and EP1173582, which are incorporated herein by reference for this purpose. Glyphosate resistance is also imparted to plants that express a gene that encodes a glyphosate oxido-reductase enzyme, as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. No. 7,462,481. A DNA molecule encoding a mutant aroA gene can be obtained under ATCC Accession No. 39256, and the nucleotide sequence of the mutant gene is disclosed in U.S. Pat. No. 4,769,061 to Comai. European Patent Appl. No. 0 333 033 to Kumada, et al. and U.S. Pat. No. 4,975,374 to Goodman, et al., disclose nucleotide sequences of glutamine synthetase genes which confer resistance to herbicides such as L-phosphinothricin. The nucleotide sequence of a PAT gene is provided in European Patent Appl. No. 0 242 246 to Leemans, et al. DeGreef, et al., *Bio/Technology*, 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall, et al., *Theon. Appl. Genet.*, 83:435 (1992).

C. An herbicide that inhibits photosynthesis, such as a triazine (psbA and gs+ genes) and a benzonitrile (nitrilase gene). Przibila, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

D. Acetohydroxy acid synthase, which has been found to make plants that express this enzyme resistant to multiple types of herbicides, has been introduced into a variety of plants. See, Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)); genes for glutathione reductase and superoxide dismutase (Aono, et al., *Plant Cell Physiol.*, 36:1687 (1995)); and genes for various phosphotransferases (Datta, et al., *Plant Mol. Biol.*, 20:619 (1992)).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes (A-E) can be introduced into the claimed grapevine cultivar through a variety of means including but not limited to transformation and crossing.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See, Knultzon, et al., *Proc. Natl. Acad. Sci. USA*, 89:2625 (1992).

B. Modified carbohydrate composition effected, for example, by transforming plants with a gene coding for an enzyme that alters the branching pattern of starch, or a gene altering thioredoxin, such as NTR and/or TRX (see, U.S. Pat. No. 6,531,648, which is incorporated by reference for this purpose), and/or a gamma zein knock out or mutant, such as cs27 or TUSC27 or en27 (see, U.S. Pat. No. 6,858,778, and U.S. Publ. Nos. 2005/0160488 and 2005/0204418, which are incorporated by reference for this purpose). See, Shiroza, et al., *J. Bacteriol.*, 170:810 (1988) (nucleotide sequence of *Streptococcus mutans* fructosyltransferase gene); Steinmetz, et al., *Mol. Gen. Genet.*, 200:220 (1985) (nucleotide sequence of *Bacillus subtilis* levansucrase gene); Pen, et al., *Bio/Technology*, 10:292 (1992) (production of transgenic plants that express *Bacillus licheniformis* alpha-amylase); Elliot, et al., *Plant Molec. Biol.*, 21:515 (1993) (nucleotide sequences of tomato invertase genes); Sogaard, et al., *J. Biol. Chem.*, 268: 22480 (1993) (site-directed mutagenesis of barley alpha-amylase gene); Fisher, et al., *Plant Physiol.*, 102:1045 (1993) (maize endosperm starch branching enzyme II); WO 99/10498 (improved digestibility and/or starch extraction through modification of UDP-D-xylose 4-epimerase, Fragile 1 and 2, Ref 1, HCHL, C4H); U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

C. Altered antioxidant content or composition, such as alteration of tocopherol or tocotrienols. See, for example, U.S. Pat. Nos. 6,787,683, 7,154,029, WO 00/68393 (involving the manipulation of antioxidant levels through alteration of a phytl prenyl transferase (ppt)); WO 03/082899 (through alteration of a homogentisate geranyl geranyl transferase (hggt)).

4. Genes that Create a Site for Site Specific DNA Integration:

This includes the introduction of FRT sites that may be used in the FLP/FRT system and/or Lox sites that may be used in the Cre/Loxp system. See, for example, Lyznik, et al., Site-Specific Recombination for Genetic Engineering in Plants, *Plant Cell Rep*, 21:925-932 (2003) and WO 99/25821, which are hereby incorporated by reference. Other systems that may be used include the Gin recombinase of phage Mu (Maeser, et al. (1991); Vicki Chandler, The Maize Handbook, Ch. 118 (Springer-Verlag 1994)); the Pin recombinase of *E. coli* (Enomoto, et al. (1983)); and the R/RS system of the pSR1 plasmid (Araki, et al. (1992)).

5. Genes that Affect Abiotic Stress Resistance:

Genes that affect abiotic stress resistance (including but not limited to flowering, fruit development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/

013227, WO 2003/013228, WO 2003/014327, WO 2004/031349, WO 2004/076638, WO 98/09521, and WO 99/38977 describing genes, including CBF genes and transcription factors effective in mitigating the negative effects of freezing, high salinity, and drought on plants, as well as conferring other positive effects on plant phenotype; U.S. Publ. No. 2004/0148654 and WO 01/36596, where abscisic acid is altered in plants resulting in improved plant phenotype, such as increased yield and/or increased tolerance to abiotic stress; WO 2000/006341, WO 04/090143, U.S. Pat. Nos. 7,531,723 and 6,992,237, where cytokinin expression is modified resulting in plants with increased stress tolerance, such as drought tolerance, and/or increased yield. See also, WO 02/02776, WO 2003/052063, JP 2002281975, U.S. Pat. No. 6,084,153, WO 01/64898, and U.S. Pat. Nos. 6,177,275 and 6,107,547 (enhancement of nitrogen utilization and altered nitrogen responsiveness). For ethylene alteration, see, U.S. Publ. Nos. 2004/0128719, 2003/0166197, and WO 2000/32761. For plant transcription factors or transcriptional regulators of abiotic stress, see, e.g., U.S. Publ. Nos. 2004/0098764 or 2004/0078852.

Other genes and transcription factors that affect plant growth and agronomic traits, such as yield, flowering, plant growth, and/or plant structure, can be introduced or introgressed into plants. See, e.g., WO 97/49811 (LHY), WO 98/56918 (ESD4), WO 97/10339, U.S. Pat. No. 6,573,430 (TFL), U.S. Pat. No. 6,713,663 (FT), U.S. Pat. Nos. 6,794,560, 6,307,126 (GAI), WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht), WO 2004/076638, and WO 004/031349 (transcription factors).

Methods for Grapevine Transformation

Numerous methods for plant transformation have been developed including biological and physical plant transformation protocols. See, for example, Miki, et al., "Procedures for Introducing Foreign DNA into Plants," in *Methods in Plant Molecular Biology and Biotechnology*, Glick and Thompson Eds., CRC Press, Inc., Boca Raton, pp. 67-88 (1993). In addition, expression vectors and in-vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993).

A. *Agrobacterium*-mediated Transformation—One method for introducing an expression vector into plants is based on the natural transformation system of *Agrobacterium*. See, for example, Horsch, et al., *Science*, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Reports*, 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microproj ectile-mediated transformation where DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford, et al., *Part. Sci. Technol.*, 5:27 (1987); Sanford, J. C., *Trends Biotech.*, 6:299 (1988); Klein, et al., *Bio/Tech.*, 6:559-563 (1988); Sanford, J. C., *Physiol Plant*, 7:206 (1990); Klein, et al., *Biotechnology*, 10:268 (1992). See also, U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang, et al., *Bio/Technology*, 9:996 (1991). Alternatively, liposome and spheroplast fusion have been used to introduce expression vectors into plants. Deshayes, et al., *EMBO J.*, 4:2731 (1985); Christou, et al., *Proc Natl. Acad. Sci. USA*, 84:3962 (1987). Direct uptake of DNA into protoplasts using $CaCl_2$ precipitation, polyvinyl alcohol or poly-L-ornithine have also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described (Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994)).

Following transformation of grapevine target tissues, expression of the above-described selectable marker genes allows for preferential selection of transformed cells, tissues, and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular grapevine line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Gene Conversions

When the term "grapevine plant" is used in the context of the present invention, this also includes any gene conversions of that variety. The term "gene converted plant" as used herein refers to those grapevine plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental grapevine plant which contributes the gene for the desired characteristic is termed the "nonrecurrent" or "donor parent." This terminology refers to the fact that the nonrecurrent parent is used one time in the backcross protocol and therefore does not recur. The parental grapevine plant to which the gene or genes from the nonrecurrent parent are transferred is known as the recurrent parent as it is used for several rounds in the backcrossing protocol. Poehlman &

Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a grapevine plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Introduction of a New Trait or Locus into Grapevine Cultivar JB05-22-3-27

Cultivar JB05-22-3-27 represents a new base genetic variety into which a new locus or trait may be introgressed. Direct transformation and backcrossing represent two important methods that can be used to accomplish such an introgression. The term backcross conversion and single locus conversion are used interchangeably to designate the product of a backcrossing program.

Tissue Culture and Embryo Rescue

Further reproduction of the variety can occur by tissue culture, embryo rescue and regeneration. Tissue culture and embryo rescue of various tissues of grapevine and regeneration of plants therefrom is well known and widely published. For example, reference may be had to Emershad, R. L. and D. W. Ramming, 1984, In-ovulo embryo culture of *Vitis vinifera* L. cv. 'Thompson Seedless', Amer. J. Bot. 71:873-877; Emershad, R. L., D. W. Ramming and M. D. Serpe, 1989, In-ovulo embryo development and plant formation from stenospermic genotypes of *Vitis vinifera*, Amer. J. Bot. 76:397-402; Gray, D. J., L. C. Fisher and J. A. Mortensen, 1987, Comparison of methodologies for in-ovulo embryo rescue of seedless grapes, HortSci. 22(6):1334-1335; Komatsuda, T., et al., *Crop Sci.*, 31:333-337 (1991); Stephens, P. A., et al., *Theon. Appl. Genet.*, 82:633-635 (1991); Komatsuda, T., et al., *Plant Cell, Tissue and Organ Culture,* 28:103-113 (1992); Dhir, S., et al., *Plant Cell Reports,* 11:285-289 (1992); Pandey, P., et al., *Japan J. Breed.*, 42:1-5 (1992); and Shetty, K., et al., *Plant Science,* 81:245-251 (1992); as well as U.S. Pat. No. 5,024,944, issued Jun. 18, 1991 to Collins, et al., and U.S. Pat. No. 5,008,200, issued Apr. 16, 1991 to Ranch, et al. Thus, another aspect of this invention is to provide cells which upon growth and differentiation produce grapevine plants having the physiological and morphological characteristics of grapevine cultivar JB05-22-3-27.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a grapevine plant by crossing a first parent grapevine plant with a second parent grapevine plant wherein the first or second parent grapevine plant is a grapevine plant of cultivar JB05-22-3-27. Further, both first and second parent grapevine plants can come from grapevine cultivar JB05-22-3-27. Thus, any such methods using grapevine cultivar JB05-22-3-27 are part of this invention: selfing, backcrosses, hybrid production, crosses to populations, and the like. All plants produced using grapevine cultivar JB05-22-3-27 as at least one parent are within the scope of this invention, including those developed from cultivars derived from grapevine cultivar JB05-22-3-27. Advantageously, this grapevine cultivar could be used in crosses with other, different, grapevine plants to produce the first generation ($F_1$) grapevine hybrid seeds and plants with superior characteristics. The cultivar of the invention can also be used for transformation where exogenous genes are introduced and expressed by the cultivar of the invention. Genetic variants created either through traditional breeding methods using grapevine cultivar JB05-22-3-27 or through transformation of cultivar JB05-22-3-27 by any of a number of protocols known to those of skill in the art are intended to be within the scope of this invention.

The following describes breeding methods that may be used with grapevine cultivar JB05-22-3-27 in the development of further grapevine plants. One such embodiment is a method for developing cultivar JB05-22-3-27 progeny grapevine plants in a grapevine plant breeding program comprising: obtaining the grapevine plant, or a part thereof, of cultivar JB05-22-3-27, utilizing said plant or plant part as a source of breeding material, and selecting a grapevine cultivar JB05-22-3-27 progeny plant with molecular markers in common with cultivar JB05-22-3-27 and/or with morphological and/or physiological characteristics selected from the characteristics listed in Table 1. Breeding steps that may be used in the grapevine plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of grapevine cultivar JB05-22-3-27 progeny grapevine plants, comprising crossing cultivar JB05-22-3-27 with another grapevine plant, thereby producing a population of grapevine plants, which, on average, derive 50% of their alleles from grapevine cultivar JB05-22-3-27. A plant of this population may be selected and repeatedly selfed or sibbed with a grapevine cultivar resulting from these successive filial generations. One embodiment of this invention is the grapevine cultivar produced by this method and that has obtained at least 50% of its alleles from grapevine cultivar JB05-22-3-27.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes grapevine cultivar JB05-22-3-27 progeny grapevine plants comprising a combination of at least two cultivar JB05-22-3-27 traits selected from the group consisting of those listed in Table 1 or the cultivar JB05-22-3-27 combination of traits listed in the Summary of the Invention, so that said progeny grapevine plant is not significantly different for said traits than grapevine cultivar JB05-22-3-27 as determined at the 5% significance level when grown in the same environmental conditions. Using techniques described herein, molecular markers may be used to identify said progeny plant as a grapevine cultivar JB05-22-3-27 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of grapevine cultivar JB05-22-3-27 may also be characterized through their filial relationship with grapevine cultivar JB05-22-3-27, as for example, being within a certain number of breeding crosses of grapevine cultivar JB05-22-3-27. A breeding cross is a cross made to introduce new genetics into the progeny, and is distinguished from a cross, such as a self or a sib cross, made to select among existing genetic alleles. The lower the number of breeding crosses in the pedigree, the closer the relationship between grapevine cultivar JB05-22-3-27 and its progeny. For example, progeny produced by the methods described herein may be within 1, 2, 3, 4, or 5 breeding crosses of grapevine cultivar JB05-22-3-27.

The development of commercial grapevine cultivars requires the development of grapevine varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into grapevine varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

As used herein, the term "plant" includes plant cells, plant protoplasts, plant cell tissue cultures from which grapevine plants can be regenerated, plant calli, plant clumps, and plant cells that are intact in plants or parts of plants, such as leaves, pollen, embryos, cotyledons, hypocotyl, roots, root tips, anthers, pistils, flowers, ovules, fruits, seeds, stems, and the like.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the SCARLET TANAGER proprietary GRAPEVINE PLANT NAMED JB05-22-3-27 disclosed above and recited in the appended claims has been made with the National Collections of Industrial Food and Marine Bacteria (NCIMB), Ferguson Building, Craibstone Estate, Bucksburn, Aberdeen AB21 9YA, Scotland, United Kingdom. The date of deposit was Mar. 12, 2015. The deposit of 20 vials of live plant tissue culture was taken from the same deposit maintained by SCARLET TANAGER since prior to the filing date of this application. All restrictions will be irrevocably removed upon granting of a patent, and the deposit is intended to meet all of the requirements of 37 C.F.R. §§1.801-1.809. The NCIMB Accession Number is NCIMB 42384. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A grapevine plant or plant part of grapevine cultivar JB05-22-3-27, wherein a representative sample of said plant was deposited under NCIMB No. 42384.

2. A grapevine plant, or a part thereof, produced by growing the deposited sample of claim 1.

3. A grapevine plant, or a part thereof, clonally propagated from the plant of claim 1.

4. A tissue culture of cells produced from protoplasts or cells from the plant of claim 1, wherein said cells or protoplasts are produced from a plant part selected from the group consisting of leaf, pollen, embryo, cotyledon, hypocotyl, meristematic cell, root, root tip, pistil, anther, flowers, stem and fruit.

5. A grapevine plant regenerated from the tissue culture of claim 4, wherein said plant has all of the physiological and morphological characteristics of grapevine cultivar JB05-22-3-27.

6. A method for producing a grapevine plant, said method comprising crossing two grapevine plants, harvesting the resultant seed or embryo and growing said seed or embryo into a mature grapevine plant, wherein at least one grapevine plant is the grapevine plant of claim 1.

7. The method of claim 6, wherein one of said grapevine plants is transgenic and the other is grapevine cultivar JB05-22-3-27.

8. A method of producing an herbicide resistant grapevine plant, wherein said method comprises introducing a gene conferring herbicide resistance into the plant of claim 1 via transformation.

9. An herbicide resistant grapevine plant produced by the method of claim 8, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

10. A method of producing a pest or insect resistant grapevine plant, wherein said method comprises introducing a gene conferring pest or insect resistance into the grapevine plant of claim 1 via transformation.

11. A pest or insect resistant grapevine plant produced by the method of claim 10.

12. The grapevine plant of claim 11, wherein the gene encodes a *Bacillus thuringiensis* (Bt) endotoxin.

13. A method of producing a disease resistant grapevine plant, wherein said method comprises introducing a gene which confers disease resistance into the grapevine plant of claim 1 via transformation.

14. A disease resistant grapevine plant produced by the method of claim 13.

15. A method of producing a grapevine plant with modified fatty acid metabolism or modified carbohydrate metabolism, wherein the method comprises introducing a gene encoding a protein selected from the group consisting of phytase, fructosyltransferase, levansucrase, α-amylase, invertase, starch branching enzyme and DNA encoding an antisense of stearyl-ACP desaturase into the grapevine plant of claim 1 via transformation.

16. A grapevine plant having modified fatty acid metabolism or modified carbohydrate metabolism produced by the method of claim 15.

17. A method of producing a commodity plant product, said method comprising obtaining the plant of claim 1, or a part thereof, and producing the commodity plant product from said plant or plant part thereof, wherein said commodity plant product is selected from the group consisting of whole grapes, raisins, fruit leather, paste, puree, freeze-dried fruits, nutraceutical preparations, wine, juice, jam and jelly.

18. The commodity plant product produced by the method of claim 17, wherein the commodity plant product comprises at least a first cell of said plant or plant part of grapevine cultivar JB05-22-3-27.

* * * * *